United States Patent
Zhang et al.

(10) Patent No.: US 9,359,384 B2
(45) Date of Patent: Jun. 7, 2016

(54) ORGANOHALOSILANE AND USE THEREOF IN ELECTROLYTES OF NON-AQUEOUS LITHIUM ION BATTERIES

(71) Applicant: Guangzhou Institute of Energy Conversion, Chinese Academy of Sciences, Guangzhou (CN)

(72) Inventors: Lingzhi Zhang, Guangzhou (CN); Hao Luo, Guangzhou (CN); Yongjin Mai, Guangzhou (CN)

(73) Assignee: GUANGZHOU INSTITUTE OF ENERGY CONVERSION, CHINESE ACADEMY OF SCIENCES, Guangzhou (CN)

( * ) Notice: Subject to any disclaimer, the term of this patent is extended or adjusted under 35 U.S.C. 154(b) by 0 days.

(21) Appl. No.: 14/675,690

(22) Filed: Mar. 31, 2015

(65) Prior Publication Data

US 2015/0203516 A1 Jul. 23, 2015

Related U.S. Application Data

(63) Continuation-in-part of application No. PCT/CN2012/084192, filed on Nov. 7, 2012.

(30) Foreign Application Priority Data

Oct. 15, 2012 (CN) .......................... 2012 1 0389659

(51) Int. Cl.
| | | |
|---|---|---|
| C07F 7/10 | (2006.01) |
| C07F 7/08 | (2006.01) |
| C07F 7/12 | (2006.01) |
| H01M 10/0567 | (2010.01) |
| H01M 10/0569 | (2010.01) |
| C07F 7/18 | (2006.01) |
| H01M 10/0525 | (2010.01) |

(52) U.S. Cl.
CPC ............... *C07F 7/0818* (2013.01); *C07F 7/083* (2013.01); *C07F 7/12* (2013.01); *C07F 7/184* (2013.01); *H01M 10/0525* (2013.01); *H01M 10/0567* (2013.01); *H01M 10/0569* (2013.01); *H01M 2300/0028* (2013.01); *Y02E 60/122* (2013.01)

(58) Field of Classification Search
USPC ................................... 556/423, 445, 452, 413
See application file for complete search history.

(56) References Cited

U.S. PATENT DOCUMENTS

2009/0286157 A1* 11/2009 Chen et al. .................... 429/209

FOREIGN PATENT DOCUMENTS

WO    WO 2013/116836 A1 *  8/2013 ............. C08G 77/18

\* cited by examiner

*Primary Examiner* — Fereydoun G Sajjadi
*Assistant Examiner* — Pancham Bakshi
(74) *Attorney, Agent, or Firm* — Matthias Scholl P.C.; Matthias Scholl

(57) ABSTRACT

An organohalosilane represented by formula I, where $R_1$, $R_2$, and $R_3$ independently, at each occurrence, represent —$(CH_2)_xCH_3$ where x is an integer from 0 to 5, or a halogen substituent where the halogen is F or Cl, and at least one substituent from $R_1$, $R_2$, and $R_3$ is the halogen substituent; $R_4$ is a $C_1$-$C_5$ alkoxyl or a tertiary amine represented by —$NR_5R_6$, where $R_5$ and $R_6$ independently, at each occurrence, represent a same or different $C_1$-$C_5$ alkyl; m is an integer from 1 to 20; and n is an integer from 0 to 5. The organohalosilane is used for preparation of an electrolyte solution of a non-aqueous lithium ion battery.

2 Claims, 3 Drawing Sheets

ORGANOHALOSILANE AND USE THEREOF IN ELECTROLYTES OF NON-AQUEOUS LITHIUM ION BATTERIES

CROSS-REFERENCE TO RELATED APPLICATIONS

This application is a continuation-in-part of International Patent Application No. PCT/CN2012/084192 with an international filing date of Nov. 7, 2012, designating the United States, now pending, and further claims priority benefits to Chinese Patent Application No. 201210389659.1 filed Oct. 15, 2012. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND OF THE INVENTION

1. Field of the Invention

The invention relates to an organohalosilane and electrolytes of non-aqueous lithium ion batteries comprising the same.

2. Description of the Related Art

Typically, non-aqueous lithium ion batteries employ organic carbonate compounds as a non-aqueous solvent. However, carbonate compounds have high flammability. Studies show that organosilicon compounds exhibit excellent thermal stability, high conductivity, non-toxicity, low flammability and high decomposition voltage, so they have aroused interest for use in organosilicon electrolyte materials.

SUMMARY OF THE INVENTION

In view of the above-described problems, it is one objective of the invention to provide an organohalosilane that has a wide application scope.

To achieve the above objective, in accordance with one embodiment of the invention, there is provided an organohalosilane represented by formula I,

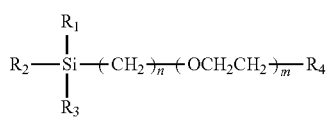

wherein $R_1$, $R_2$, and $R_3$ independently, at each occurrence, represent —$(CH_2)_xCH_3$ where x is an integer from 0 to 5, or a halogen substituent where the halogen is F or Cl, and at least one substituent from $R_1$, $R_2$, and $R_3$ is the halogen substituent; $R_4$ is a $C_1$-$C_5$ alkoxyl or tertiary amine represented by —$NR_5R_6$, where $R_5$ and $R_6$ independently, at each occurrence, represent a same or different $C_1$-$C_5$ alkyl, m is an integer from 1 to 20, and n is an integer from 0 to 5.

The chemical structure represented by formula I comprises a Si—F bond, which can improve the stability of the electrochemical properties. The polyether chain in the chemical structure provides a complexation site for lithium ions thereby facilitating the ion transport and improving the battery performance.

The invention further provides a method for preparation of an electrolyte solution of a non-aqueous lithium ion battery comprising adding the organohalosilane represented by formula I in the process of preparation.

In a class of this embodiment, the organohalosilane represented by formula I is used as a non-aqueous solvent or an additive of the electrolyte solution. The electrolyte solution of the non-aqueous lithium ion battery comprises a fluorine-containing alkali metal salt, a high dielectric constant or low boiling point organic solvent, and the organohalosilane represented by formula I.

Advantages according to embodiments of the invention are summarized as follows. The organohalosilane has a wide electrochemical window, and can be used as a non-aqueous solvent or an additive of the electrolyte solution thereby forming a stable SEI membrane on the surface of the electrode, or used as an electrolyte material for the non-aqueous lithium ion battery with arbitrary shape and structure, or applied to a power storage device (such as electrolytic capacitor and supercapacitor). The preparation method of the organohalosilane is simple, highly efficient, and easy to operate and popularize. In addition, the involved materials are easily available.

DETAILED DESCRIPTION OF THE EMBODIMENTS

Figure 1:
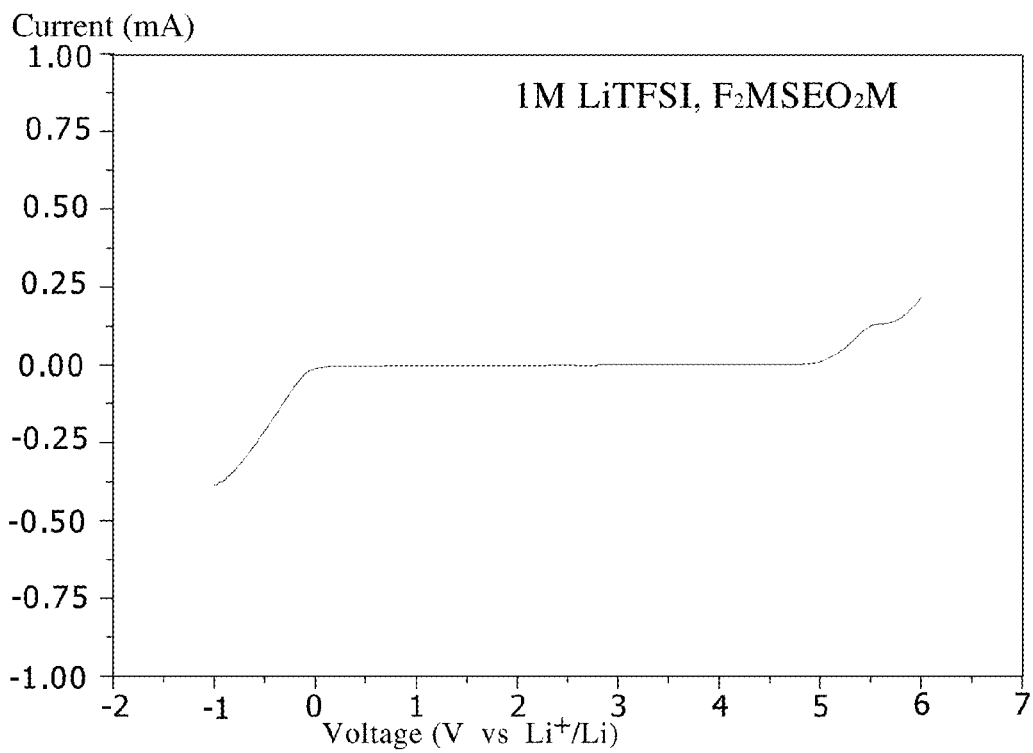
FIG. 1 shows an electrochemical window curve of a compound in Example 2 of the invention.

For further illustrating the invention, experiments detailing an organohalosilane having a polyether chain and the use thereof in electrolytes of non-aqueous lithium ion batteries are described below. It should be noted that the following examples are intended to describe and not to limit the invention.

The invention provides two methods for synthesizing an organohalosilane having a polyether chain.

The first synthesis method is summarized as follows:

Chemical reactions (1) to yield formula I

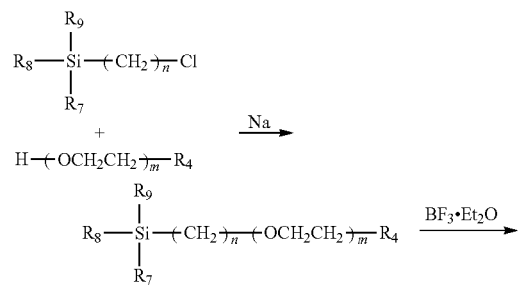

-continued

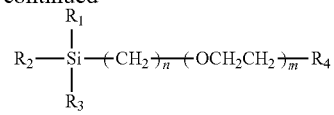

$R_1, R_2, R_3 =$ —$CH_3$, —$C_2H_5$, —$C_3H_7$, —$C_4H_9$, —$C_5H_{11}$, —$C_6H_{13}$, —$C_7H_{15}$, F, Cl etc.

$R_4 =$ —$OCH_3$, —$OC_2H_5$, —$OC_5H_{11}$, —$NR_5R_6$ etc.

$R_5, R_6 =$ —$CH_3$, —$C_2H_5$, —$C_5H_{11}$, —$C_6H_{13}$ etc.

$R_7, R_8, R_9 =$ —$(OCH_2CH_2)_m$—$R_4$, —$CH_3$, —$C_2H_5$, —$C_5H_{11}$, —$OCH_3$, —$OC_2H_5$ etc.

$m = 1\text{-}20, n = 0\text{-}5$

Specifically, an alcohol containing a polyether chain reacts with metal sodium to yield a sodium alcoholate, which reacts with a halogen silane compound for etherification, followed by a fluorination reaction in the presence of a fluorinating agent, whereby yield an organohalosilane having a polyether chain.

In this method, the molar ratio of the alcohol containing a polyether chain to metal sodium is between 1:1 and 10:1, preferably between 3:1 and 5:1. The molar ratio of the sodium alcoholate to the halogen silane compound to the fluorinating agent is between 1: 1:1 and 1:1:6, preferably, between 1:1:2 and 1:1:4.5. The etherification temperature is between 80 and 150° C. and the reaction lasts for 24 hours. The fluorination reaction temperature is between 25 and 85° C. and the reaction lasts for between 4 and 30 hours.

The organic alcohol is selected from alkoxy alcohols or amino alcohols containing a polyether chain, and the unit number of the polyether chain is between 1 and 20. The organic alcohol includes but is not limited to ethylene glycol monomethyl ether, diethylene glycol monomethyl ether, triethylene glycol monomethyl ether, tetraethylene glycol monomethyl ether, N,N-dimethyl ethanol, N,N-dimethyl diethoxy based ethanol, N,N-dimethyl-three-ethoxyethanol, N,N-dimethyl-four-ethoxyethanol.

The halogen silane compound is chlorosilane or iodine silane with a side chain comprising same or different $C_1$-$C_5$ alkyl or alkoxy, aromatic group or hydrogen atoms, including but not limited to dimethyl chlorosilane, diethyl chlorosilane, dipropyl chlorosilane, chlorosilanes dibutyl, diamyl chlorosilane, methyl dichlorosilane, ethyl dichlorosilane, propyl dichlorosilane, butyl dichlorosilane, pentyl dichlorosilane, trichlorosilane, 3-chloropropyl trimethoxysilane, 3-chloropropyl triethoxysilane, 3-chloropropyl diethoxymethylsilane, 3-chloropropyl dimethyl ethoxy silane, 3-chloro-ethyl trimethoxysilane, 3-chloro-ethyl methyl diethoxy silane, 3-chloropropyl trichlorosilane, 3-chloropropyl diethyl propyl silane, 3-chloropropyl diethoxy-butyl silane, 3-chloropropyl pentyl diethoxy silane, 3-chloropropyl allyl diethoxy silane, 3-chloropropyl ene-butyl group diethoxy silane.

The second synthesis method is summarized as follows:

Chemical reactions (2) to yield formula I

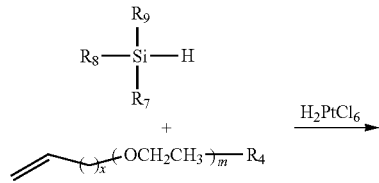

-continued

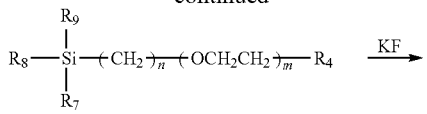

$R_1, R_2, R_3, R_7, R_8, R_9 =$ —$CH_3$, —$C_2H_5$, —$C_3H_7$, —$C_4H_9$, —$C_5H_{11}$, —$C_6H_{13}$, —$C_7H_{15}$, F, Cl etc.

$R_4 =$ —$OCH_3$, —$OC_2H_5$, —$OC_5H_{11}$, —$NR_5R_6$ etc.

$R_5, R_6 =$ —$CH_3$, —$C_2H_5$, —$C_5H_{11}$, —$C_6H_{13}$ etc.

$m = 1\text{-}20, n = 0\text{-}5, x = 1\text{-}3$.

Specifically, with platinum as a catalyst, terminal olefin with a polyether chain reacts with a halogen silane compound for hydrosilication, followed by a fluorination reaction in the presence of a fluorinating agent, whereby yield an organohalosilane having a polyether chain.

In the second method, the molar ratio of the terminal olefin to halogen silane compound to the catalyst to the fluorinating agent is between 1:1.05:0.05:1 and 1:1.05: 0.05:6, preferably, between 1:1.05:0.05:2 and 1:1.05:0.05:4.5. The hydrosilication temperature is between 50 and 100° C. and the reaction lasts for 24 hours. The fluorination reaction temperature is between 20 and 35° C. and the reaction lasts for between 4 and 24 hours.

The platinum catalyst is selected from chloroplatinic acid, platinum oxide, platinum black, or Karstedt catalyst.

The fluorinating agent is selected from boron trifluoride etherate, potassium fluoride, zinc fluoride, antimony fluoride, and cesium fluoride.

The terminal olefin with a polyether chain has a chemical formula of

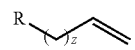

and is synthesized as follows:

Chemical reaction to yield terminal olefin

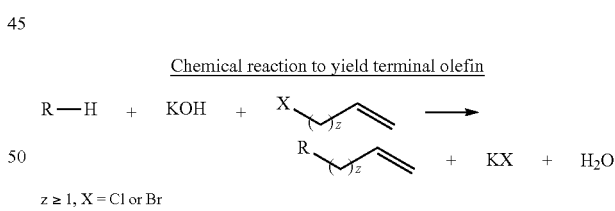

$z \geq 1, X = Cl \text{ or } Br$

Specifically, the terminal olefin with a polyether chain is synthesized by an etherification reaction between an alcohol containing a polyether chain and allyl bromide or allyl chloride under alkali condition (in the presence of potassium hydroxide or sodium hydroxide). Firstly, the alcohol reacts with excess potassium hydroxide to yield potassium alcoholate, followed by the slow addition of allyl bromide or allyl chloride in an ice-water bath. The mixture is allowed to stand for several hours at room temperature, and then filtered by suction, extracted, washed, dried and distilled to yield the terminal olefin with a polyether chain.

The following chemical formulas represent some compounds involved in Examples 1-6.

Compounds of examples 1-6

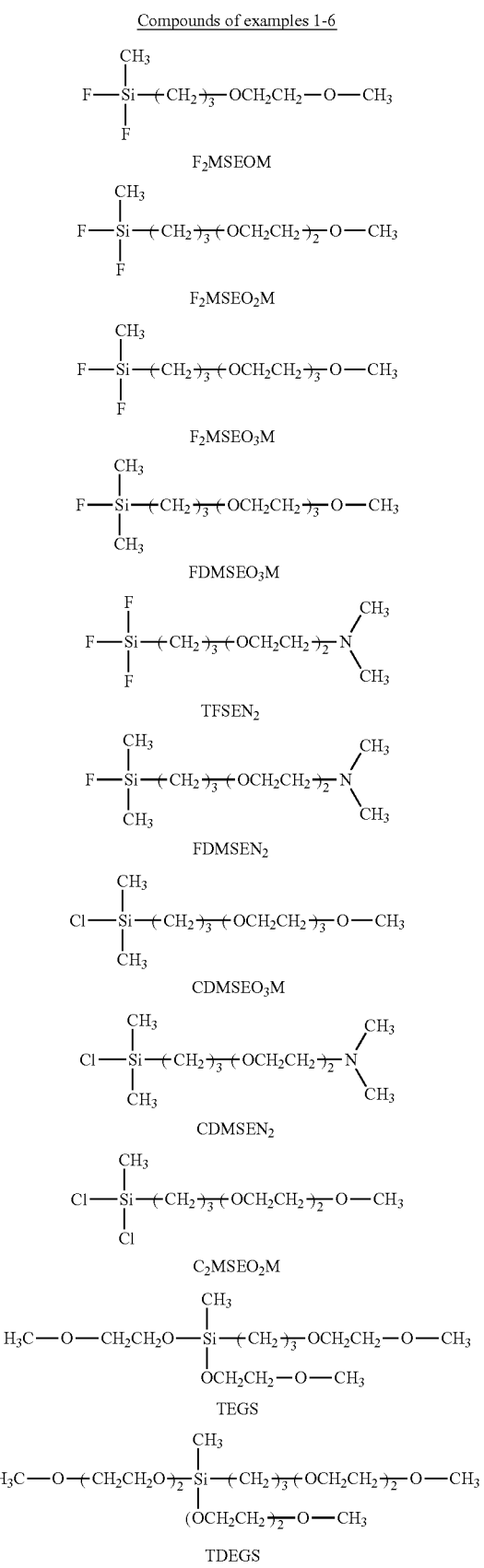

EXAMPLE 1

Preparation of 3-(methoxyethoxy) propyl-methyl-difluoro-silane ($F_2$MSEOM)

Under protection of argon, ethylene glycol monomethyl ether (61 g, 0.8 mol) was added to a two-mouthed round bottom flask (250 mL), followed by the addition of metal sodium (4.6 g, 0.2 mol) in batches. The flask was heated to 80° C. until metal sodium disappeared, and then 3-chloropropyl diethoxymethylsilane (42.1 g, 0.2 mol) was added, heated gradually to 120° C., and allowed to react for 24 hours. The reaction mixture was cooled to room temperature, filtered by suction, distilled under reduced pressure, thus yielding 44.5 g of colorless liquid, that is, 3-(methoxyethoxy) propyl methyl bis(methoxyethoxy) silane, b.p.: 135° C. (3 mmHg), yield: 60%. Under protection of argon, 98% of boron trifluoride etherate (29.43 g, 0.203 mol) was added dropwise to 3-(methoxyethoxy) propyl methyl bis(methoxyethoxy) silane (21.03 g, 0.067 mol). The resulting mixture was allowed to react at room temperature for 30 hours, and then distilled under reduced pressure to yield 11.74 of colorless transparent liquid, that is, 3-(methoxyethoxy) propyl-methyl-difluoro-silane, b.p.: 34.5° C. (3 mmHg), yield: 87%.

3-(methoxyethoxy)propyl methyl bis(methoxyethoxy)silane (TEGS)

$^1$H-NMR (600 MHz, CDCl$_3$), δ: 3.80(t, 4H, Si—O—CH$_2$, J=4.92 Hz), 3.53(m, 4H, Si—O—C CH$_2$), 3.45(t, 4H, Si—C—C—C—O—CH$_2$—CH$_2$, J=4.95 Hz), 3.40(t, 2H, Si—C—C—CH$_2$, J=7.02 Hz), 3.36(s, 3H, Si—C—C—C—O—C—C—O—CH$_3$), 3.35(s, 6H, Si—O—C—C—O—CH$_3$), 1.65(m, 2H, Si—C—CH$_2$), 0.62(m, 2H, Si—CH$_2$), 0.12(s, 3H, Si—CH$_3$).

$^{13}$C-NMR(300 MHz, CDCl$_3$), δ: 73.87, 73.84, 71.97, 69.89, 61.81, 59.04, 58.95, 22.84, 9.72, −4.96.

3-(methoxyethoxy)propyl-methyl-difluoro-silane $^1$H-NMR(600 MHz, CDCl$_3$), δ: 3.56(m, 2H, CH$_2$—O—CH$_3$), 3.52(m, 2H, Si—C—C—C—O—CH$_2$, J=1.8 Hz), 3.44(t, 2H, Si—C—C—CH$_2$, J=6.36 Hz), 3.37(s, 3H, —O—CH$_3$), 1.74(m, 2H, Si—C—CH$_2$), 0.82(m, 2H, Si—CH$_2$), 0.33(dd, 3H, Si—CH$_3$, J=6.27 Hz).

$^{13}$C-NMR(300 MHz, CDCl$_3$)), δ: 72.60, 71.85, 70.03, 58.99, 21.87, 10.04(t, J=30.64 Hz), −4.25(t, J=32.28 Hz).

EXAMPLE 2

Preparation of 3-(methoxydiethoxy)propyl-methyl-difluoro-silane($F_2$MSEO$_2$M)

Under protection of argon, diethylene glycol monomethyl ether (74.4 g, 0.62 mol) was added to a two-mouthed round bottom flask (250 mL), followed by the addition of metal sodium (7 g, 0.3 mol) in batches. The flask was heated to 80° C. until metal sodium disappeared, and then 3-chloropropyl diethoxymethylsilane (62.7 g, 0.29 mol) was added, heated gradually to 120° C., and allowed to react for 24 hours. The reaction mixture was cooled to room temperature, filtered by suction, distilled under reduced pressure, thus yielding 58.8 g of colorless liquid, that is, 3-(methoxydiethoxy) propyl methyl bis(methoxydiethoxy) silane, b.p.: 170° C. (3 mmHg), yield: 65%. Under protection of argon, 46.6% of boron trifluoride etherate (29.43 g, 0.09 mol) was added dropwise to 40 mL of a toluene solution comprising 3-(methoxydiethoxy)

propyl methyl bis(methoxydiethoxy) silane (15.9 g, 0.03 mol). The resulting mixture was heated to 80° C. and allowed to react for 24 hours, and then distilled under reduced pressure to yield 3.47 of colorless transparent liquid, that is, 3-(methoxydiethoxy) propyl-methyl-difluoro-silane, b.p.: 67° C. (3 mmHg), yield: 40%.

3-(methoxydiethoxy)propyl methyl bis(methoxydiethoxy)silane(TDEGS)

$^1$H-NMR(600 MHz, CDCl$_3$), δ: 3.78(t, 4H, Si—O—CH$_2$, J=5.22 Hz), 3.58(m, 8H, Si—C—C—C—O—CH$_2$—CH$_2$—O—CH$_2$—CH$_2$), 3.50(m, 12H, Si—O—C—CH$_2$—O—CH$_2$—CH$_2$), 3.36(t, 2H, Si—C—C—CH$_2$, J=6.9 Hz), 3.32(s, 9H, O—CH$_3$), 1.59(m, 2H, Si—C—CH$_2$), 0.57(m, 2H, Si—CH$_2$), 0.07(s, 3H, Si—CH$_3$).

$^{13}$C-NMR(300 MHz, CDCl$_3$), δ: 73.64, 72.28, 71.8, 70.49, 70.38, 69.84, 61.71, 58.84, 22.73, 9.65, −5.07.

3-(methoxydiethoxy)propyl-methyl-difluoro-silane $^1$H-NMR(600 MHz, CDCl$_3$), δ: 3.63(m, 4H, Si—C—C—C—O—C—CH$_2$—O—CH$_2$), 3.59(m, 2H, Si—C—C—C—O—C—C—O—C—CH$_2$), 3.54(m, 2H, Si—C—C—C—O—CH$_2$), 3.44(t, 2H, Si—C—C—CH$_2$, J=6.3 Hz), 3.36(s, 3H, O—CH$_3$), 1.72(m, 2H, Si—C—CH$_2$), 0.82(m, 2H, Si—CH$_2$), 0.33(t, 3H, Si—CH$_3$, J=6.27 Hz).

$^{13}$C-NMR(300 MHz, CDCl$_3$), δ: 72.53, 71.94, 70.54, 70.51, 70.09, 59.00, 21.91, 10.05(t, J=30.72 Hz), −4.21(t, J=32.49 Hz).

EXAMPLE 3

Preparation of 3-(methoxytriethoxy)propyl-methyl-difluoro-silane(F$_2$MSEO$_3$M)

Under protection of argon, triethylene glycol monomethyl ether (149.91 g, 0.91 mol) was added to a two-mouthed round bottom flask (250 mL), followed by the addition of metal sodium (7 g, 0.304 mol) in batches. The flask was heated to 80° C. until metal sodium disappeared, and then 3-chloropropyl diethoxymethylsilane (64 g, 0.304 mol) was added, heated gradually to 130° C., and allowed to react for 24 hours. The reaction mixture was cooled to room temperature, and then 200 mL of toluene and 46.5% of boron trifluoride etherate (186 g, 0.61 mol) were added dropwise. The resulting mixture was heated to 85° C. and allowed to react for 4 hours, and then cooled, filtered by suction, and distilled under reduced pressure to yield 39 g of colorless transparent liquid, that is, 3-(methoxytriethoxy) propyl-methyl-difluoro-silane, b.p.: 121° C. (3 mmHg), yield: 45%.

3-(methoxytriethoxy)propyl-methyl-difluoro-silane $^1$H-NMR(600 MHz, CDCl$_3$), δ: 3.63(m, 8H, CH$_2$—O—CH$_2$CH$_2$—O—CH$_2$, J=1.8 Hz), 3.56(m, 2H, CH$_2$—O—CH$_3$, J=1.8 Hz), 3.52(m, 2H, Si—C—C—C—O—CH$_2$, J=1.8 Hz), 3.43(t, 2H, Si—C—C—CH$_2$, J=6.3 Hz), 3.36(s, 3H, C—O—C—C—O—CH$_2$), 1.71(tt, 2H, Si—C—CH$_2$, J=7.86 Hz), 0.81(dd, 2H, Si—CH$_2$, J=5.1 Hz), 0.32(dd, 3H, Si—CH$_2$, J=6.3 Hz)

$^{13}$C-NMR(300 MHz, CDCl$_3$), δ: 72.50, 71.92, 70.58, 70.56, 70.49, 70.48, 70.08, 58.97, 21.90, 10.04(t, J=30 Hz), −4.22(t, J=30 Hz).

EXAMPLE 4

3-(methoxytriethoxy)propyl-dimethyl-fluorosilane (FDMSEO$_3$M)

Under protection of argon, triglycol allyl methyl ether (25.14 g, 0.123 mol) was added to a two-mouthed round bottom flask (250 mL), followed by the addition of chloroplatinic acid (0.1 g) in batches. The flask was placed in an ice-water bath and dimethylchlorosilane (14.0 g, 0.148 mol) was added dropwise, then heated gradually to 70° C., and allowed to react for 24 hours. The reaction mixture was cooled to room temperature, distilled under reduced pressure, thus yielding 19.73 g of colorless liquid, that is, 3-(methoxytriethoxy) propyl dimethyl chlorosilane, b.p.: 112° C. (3 mmHg), yield: 54%. Under protection of argon, 3-(methoxytriethoxy) propyl dimethyl chlorosilane (19.73 g, 0.066 mol) was dissolved in 80 mL of anhydrous acetonitrile, and solid potassium fluoride (7.66 g, 1.32 mol) was added, stirred for 18 hours at room temperature, then filtered, distilled under reduced pressure to yield 15.0 of colorless transparent liquid, that is, 3-(methoxytriethoxy) propyl-dimethyl-fluorosilane, b.p.: 98° C. (3 mmHg), yield: 79%.

3-(methoxytriethoxy)propyl dimethyl chlorosilane(CDMSEO$_3$M)

$^1$H-NMR(600 MHz, CDCl$_3$), δ: 3.64(m, 8H, CH$_2$—O—CH$_2$), 3.56(m, 4H, CH$_2$—O—CH$_2$, J=1.8 Hz), 3.46(t, 2H, Si—C—C—CH$_2$, J=6.36 Hz), 3.37(s, 3H, —O—CH$_3$), 1.69(m, 2H, Si—C—CH$_2$), 0.83(m, 2H, Si—CH$_2$—C), 0.40(s, 6H, Si—CH$_3$).

3-(methoxytriethoxy)propyl-dimethyl-fluorosilane $^1$H-NMR(600 MHz, CDCl$_3$), δ: 3.63(m, 8H, CH$_2$—O—CH$_2$), 3.55(m, 4H, CH$_2$—O—CH$_2$, J=1.8 Hz), 3.42(t, 2H, Si—C—C—CH$_2$, J=6.84 Hz), 3.36(s, 3H, —O—CH$_3$), 1.65 (m, 2H, Si—C—CH$_2$), 0.67(m, 2H, Si—CH$_2$—C), 0.20(d, 6H, Si—CH$_3$, J=7.5 Hz).

$^{13}$C-NMR(300 MHz, CDCl$_3$)), δ: 73.51, 71.92, 70.60, 70.58, 70.50, 70.03, 58.98, 22.76, 12.67(d, J=28.17 Hz), −1.5 (d, J=29.85 Hz).

EXAMPLE 5

Preparation of N,N-dimethyl diethoxy propyl trifluoro silane (TFSEN$_2$)

Under protection of argon, N,N-dimethyl-diethoxyethanol (53.42 g, 0.40 mol) was added to a two-mouthed round bottom flask (250 mL), followed by the addition of metal sodium (2.3 g, 0.1 mol) in batches. The flask was heated to 80° C. until metal sodium disappeared, and then 3-chloropropyl triethoxysilane (24.08 g, 0.1 mol) was added, heated gradually to 150° C., and allowed to react for 24 hours. The reaction mixture was cooled to room temperature, filtered by suction, distilled under reduced pressure, thus yielding 41.9 g of colorless liquid, that is, N,N-dimethyl-diethoxypropyl tri(N, N-dimethyl-diethoxy) silane, b.p.: 200° C. (3 mmHg), yield: 70%. Under protection of argon, 46.5% of boron trifluoride etherate (30.9 g, 0.101 mol) was added dropwise to 3-(methoxyethoxy) propyl methyl bis(methoxyethoxy) silane (19 g, 0.037 mol). The resulting mixture was allowed to react at room temperature for 30 hours, and then distilled under reduced pressure to yield 8 of colorless transparent liquid, that is, N,N-dimethyl diethoxy propyl trifluoro silane, b.p.: 141° C. (3 mmHg), yield: 85%.

N,N-dimethyl-diethoxypropyl tri(N,N-dimethyl-diethoxy)silane $^1$H-NMR(600 MHz, CDCl$_3$), δ: 3.82(t, 6H, Si—O—CH$_2$, J=2.94 Hz), 3.46-3.52(m, 18H, O—CH$_2$—CH$_2$—O—CH$_2$—, J=6.12 Hz), 3.33(t, 2H, Si—C—C—CH$_2$, J=6.6 Hz), 2.42(m, 8H, CH—N, J=5.58 Hz), 2.19(s, 24H, N(CH$_3$)$_2$), 1.61(dd, 2H, Si—C—CH$_2$, J=7.56 Hz), 0.59(dd, 2H, Si—CH$_2$, J=7.08 Hz).

N,N-dimethyl diethoxy propyl trifluoro silane $^1$H-NMR(600 MHz, CDCl$_3$), δ: 3.82(t, 2H, Si—C—C—C—O—CH$_2$, J=5.1 Hz), 3.61(m, 4H, CH$_2$—O—CH$_2$C—N, J=4.08 Hz), 3.47(t, 2H, Si—C—C—CH$_2$, J=5.7 Hz), 3.12(t, 2H, N—CH$_2$, J=4.74 Hz), 2.67(s, 6H, N—CH$_3$), 1.83(m, 2H, Si—C—CH$_2$, J=6.36 Hz), 1.04(m, 2H, Si—CH$_2$, J=3 Hz).
$^{13}$C-NMR(300 MHz, CDCl$_3$), δ: 71.03, 70.15, 70.05, 65.41, 57.02, 44.47, 21.84, 4.23(J=37.92 Hz).

EXAMPLE 6

Preparation of N,N-dimethyl-diethoxy propyl dimethyl fluorosilane(FDMSEN$_2$)

The product was obtained by reduced pressure distillation following the method in Example 4 except that N,N-dimethyl-diethoxy allyl ether was substituted for triglycol allyl methyl ether, in which, the intermediate product was N,N-dimethyl-diethoxy propyl dimethyl chlorosilane, a colorless transparent liquid, b.p.: 90° C. (3 mmHg), yield: 80%. The product N,N-dimethyl-diethoxy propyl dimethyl fluorosilane was a colorless transparent liquid, b.p.: 83° C. (3 mmHg), yield: 85%.

N,N-dimethyl-diethoxy propyl dimethyl chlorosilane(CDMSEN$_2$)

$^1$H-NMR(600 MHz, CDCl$_3$), δ: 3.67(m, 2H, Si—C—C—C—O—CH$_2$), 3.59(m, 4H, N—C—CH$_2$—O—CH$_2$), 3.44(t, 2H, Si—C—C—CH$_2$, J=6.69 Hz), 2.66(t, 2H, N—CH$_2$, J=5.70 Hz), 2.38(s, 6H, N(CH$_3$)$_2$), 1.67(m, 2H, Si—C—CH$_2$), 0.82(m, 2H, Si—CH$_2$), 0.40(s, 6H, Si—CH$_3$).
$^{13}$C-NMR(300 MHz, CDCl$_3$), δ: 74.14, 73.23, 70.43, 69.84, 45.14, 23.39, 15.18, 1.58, 0.26.

N,N-dimethyl-diethoxy propyl dimethyl fluorosilane $^1$H-NMR(600 MHz, CDCl$_3$), δ: 3.58(m, 6H, O—CH$_2$—CH$_2$—O—CH$_2$), 3.43(t, 2H, Si—C—C—CH$_2$, J=6.78 Hz), 2.50(t, 2H, N—CH$_2$, J=5.91 Hz), 2.25(s, 6H, N(CH$_3$)$_2$), 1.66 (m, 2H, Si—C—CH$_2$), 0.68(m, 2H, Si—CH$_2$), 0.21(d, 6H, Si—CH$_3$, J=7.50 Hz).
$^{13}$C-NMR(300 MHz, CDCl$_3$), δ: 73.50, 70.38, 70.05, 69.39, 58.81, 45.88, 22.76, 12.67(d, J=28.11 Hz), −1.50(d, J=29.82 Hz).

COMPARISON EXAMPLE 1

Preparation of 3-(methoxy diethoxy)propyl-methyl-difluoro-silane(F$_2$MSEO$_2$M)

The product was obtained by reduced pressure distillation following the method in Example 4 except that diglycol allyl methyl ether was substituted for triglycol allyl methyl ether, in which, the intermediate product was 3-(methoxy diethoxy) propyl methyl dichlorosilane, a colorless transparent liquid, b.p.: 85° C. (3 mmHg), yield: 59%. The product 3-(methoxy diethoxy) propyl-methyl-difluoro-silane was a colorless transparent liquid, b.p.: 67° C. (3 mmHg), yield: 78%.

3-(methoxy diethoxy)propyl methyl dichlorosilane(C$_2$MSEO$_2$M)

$^1$H-NMR(600 MHz, CDCl$_3$), δ: 3.59(m, 8H, O—CH$_2$—CH$_2$-0), 3.44(t, 2H, Si—C—C—CH$_2$, J=6.37 Hz), 3.37(s, 3H, O—CH$_3$, J=5.91 Hz), 1.78(m, 2H, Si—C—CH$_2$), 1.17 (m, 2H, Si—CH$_2$), 0.77(s, 3H, Si—CH$_3$).
$^{13}$C-NMR(300 MHz, CDCl$_3$), δ: 72.38, 71.94, 70.61, 70.54, 70.07, 70.04, 59.01, 22.73, 18.14, 5.17.

EXAMPLE 7

Preparation of Batteries and Tests

The compound of the invention can be applied to lithium ion batteries according to following steps.

In the invention, solvents with high dielectric-constant are not specifically designated, in general, they are common non-aqueous solvents used in conventional batteries, such as cyclic carbonate, including ethylene carbonate (EC), propylene carbonate (PC) and γ-butyrolactone (γ-BL). These cyclic carbonates can be used in the form of mixture, thereby prolonging the service life of the batteries. Low boiling point solvents are not specifically designated, which, in general, are chain carbonate, such as dimethyl carbonate (DMC), ethyl methyl carbonate (EMC), diethyl carbonate (DEC), methyl propyl carbonate (MPC), and a fatty acid ester derivative. These chain carbonates can be used in the form of mixture, thereby reducing the viscosity of the electrolyte solution, improving the solubility of the electrolyte, and improving the low temperature load of the battery.

The volume ratio of the solvents with high dielectric-constant to the low boiling point solvents is between 0:100 and 100:0, preferably, between 10:90 and 80:20, more preferably, between 15:85 and 50:50. The mixing ratio can effectively inhibit the increase of viscosity of the non-aqueous electrolytic solution, improve the degree of dissociation of the electrolyte, and improve the conductivity of the electrolyte of the lithium ion battery in the process of charge-discharge.

The electrolyte of the non-aqueous electrolytic solution is a fluorine-containing alkali metal salt, such as LiPF$_6$, LiBF$_4$, LiClO$_4$, LiAsF$_6$, LiCF$_3$SO$_3$, Li$_2$SiF$_6$. These fluorine-containing alkali metal salts can be used alone or in the form of mixture, with a concentration of between 0.1 and 3 mol/L, preferably, between 0.5 and 2 mol/L.

In the non-aqueous electrolytic solution of the invention, the volume percentage of organohalosilane containing a polyether chain is 1-100%, preferably 2-80%, more preferably 5-70%, and further preferably 40-50%. In the lithium ion battery, the application of organohalosilane containing a polyether chain facilitates the formation of a uniform and stable protective layer, and can greatly improve the efficiency of batteries. In addition, organohalosilane containing a polyether chain has a wide electrochemical window, for example, in Example 2, the synthesized F$_2$MSEO$_2$M has an electrochemical window of 0-4.95 V, as shown in FIG. 1, the three-electrode system battery comprises platinum as a working electrode and lithium metal wire as a counter electrode and a reference electrode.

The lithium ion battery of the invention comprises a cathode, an anode, a separator, and the aforementioned non-aqueous electrolyte solution.

A cathode active material, a conductive agent, a binder and a solvent are mixed for the preparation of a cathode active material composition. The composition is directly coated on an aluminum current collector and then dried to prepare a cathode plate. The cathode active material is a commonly-used lithium-containing transition metal oxide in the field, such as $LiCoO_2$, $LiMn_xO_{2x}$(x=1 or 2), $LiNi_{1-x}Mn_xO_2$ (0≤x<1), $LiNi_xCo_{1-x}O_2$(0<x<1), and $LiFePO_4$, transition metal oxide or transition metal sulfide, such as $MoS_2$, $SnS_2$, $MoO_3$, and $V_2O_5$. The cathode active material is preferably selected from lithium-containing transition metal oxides.

Similarly, an anode active material, a conductive agent, a binder and a solvent are mixed for the preparation of an anode active material composition. The composition is directly coated on a copper current collector and then dried to prepare an anode plate. The anode active material can be lithium metal, lithium alloy, carbon material capable of doping and dedoping lithium ions, tin oxide, niobium oxide, vanadium oxide, and titanium oxide capable of doping and dedoping lithium ions, or silicon capable of doping and dedoping lithium ions. Preferably, the anode active material is carbon material capable of doping and dedoping lithium ions. The carbon material is graphite or amorphous carbon, such as activated carbon, carbon fiber, carbon black, and natural graphite.

Carbon black can be used as the conductive agent. The binder can be selected from the group consisting of vinylidene fluoride/hexafluoropropene copolymer, polyvinylidene fluoride (PVDF), polyacrylonitrile, polymethyl methacrylate, polytetrafluoroethylene, or a mixture thereof, or a butadiene styrene rubber-based polymer. The solvent is N-methylpyrrolidone (NMP), acetone, or water. The usage amount of the anode/cathode active material, the conductive agent, the binder and the solvent follows the normal usage amount used in common lithium ion batteries. The separator can be any material used in common lithium ion batteries, and should have low impedance to the move of the electrolyte ion and good absorption capacity and invasion to the electrolyte. For example, the material can be selected from the group consisting of glass fiber, polyester, polyethylene, polytetrafluoroethylene or nonwoven or woven fabric made therefrom, preferably, reelable porous separator made from polyethylene or polypropylene.

The lithium ion battery of the invention is cylindrical, coin-shaped, or square in shape. The shape has no influence on the basic structure, so it can be selected as needed.

In the performance test of batteries, the electrolyte and $LiPF_6$ are from Dongguan Shanshan Battery Material Co., Ltd. The lithium plate is from China Lithium Energy. Graphite is from Hefei Kejing Materials Technology Co., Ltd. The separator is from Asashi Chemical Industry. The preparation of the electrolyte and the assembly of the battery are both carried out in the presence of argon (purity exceeding 99.999%).

$LiPF_6$ is dissolved in a mixture of PC and organohalosilane $F_2MSEO_2M$ having a polyether chain (PC:$F_2MSEO_2M$=1:1) to yield an electrolyte solution having a concentration of 1 M. Take lithium metal as an anode and graphite as a cathode, respectively, to assemble a coin-shaped battery (2025). The discharge-charge test of the battery is carried out in the Shenzhen Neware battery charge and discharge test system, with a charge-discharge voltage of 0-3 V. The battery in Example 7 is charged with a constant current of 0.1 C, and then is discharged at a constant current, with the discharge rate of 0.1 C. In addition, the cyclic voltammetry is carried out using Germany ZAHNER electrochemical workstation.

Figures 3, 4:
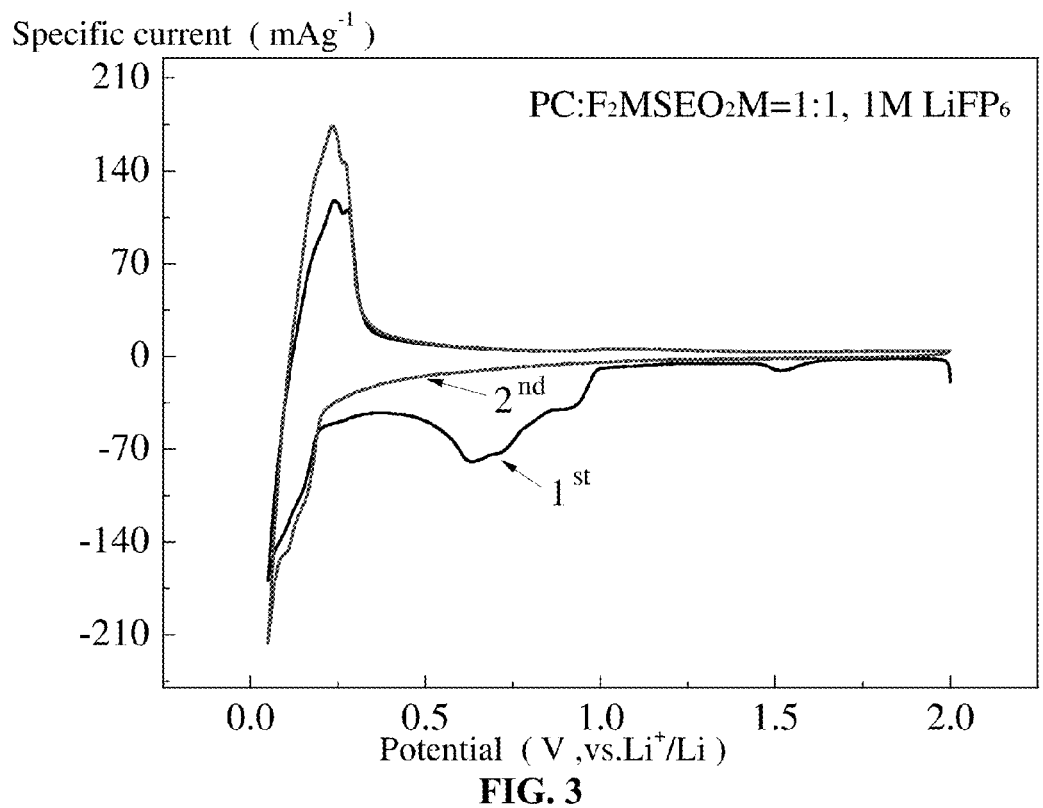
FIG. 3 shows cyclic voltammetry curves of a lithium ion battery in Example 7 of the invention.
FIG. 4 shows the first two charge-discharge curves of a lithium ion battery in Example 7 of the invention at a charge-discharge rate of 0.1 C.
Figure 5:
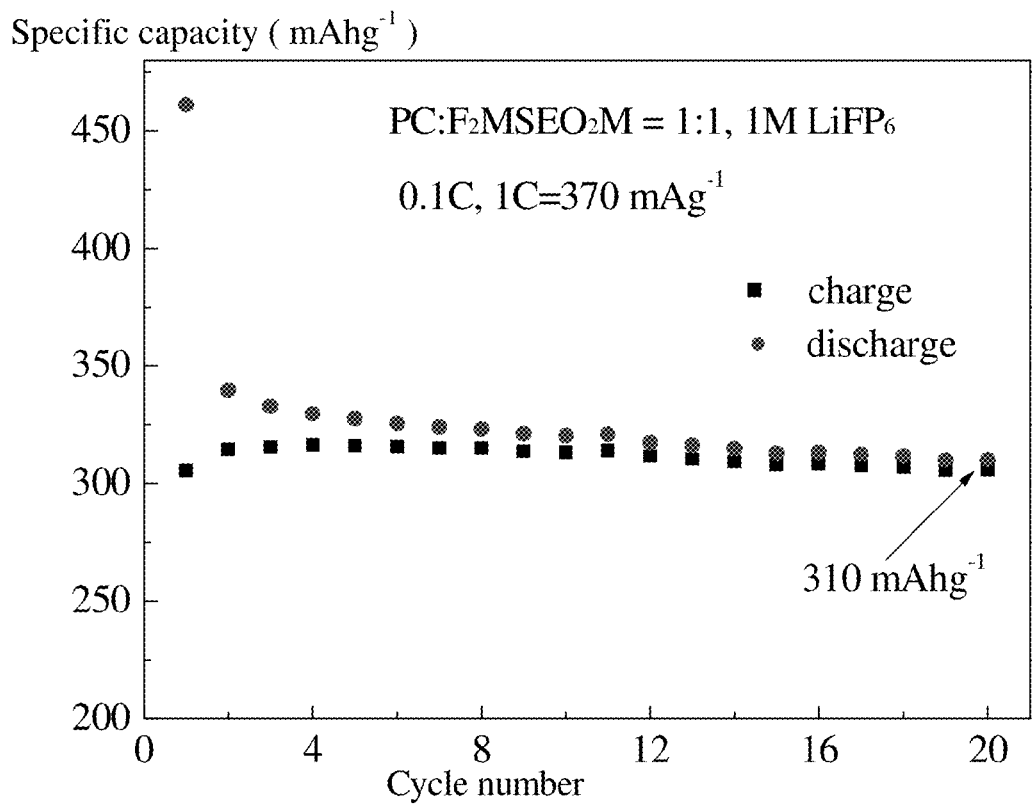
FIG. 5 shows charge-discharge cycle performance curves of a lithium ion battery in Example 7 of the invention at a charge-discharge rate of 0.1 C.

FIG. 3 shows cyclic voltammetry curves of a lithium ion battery in Example 7 of the invention; FIG. 4 shows the first two charge-discharge curves of a lithium ion battery in Example 7 of the invention at a charge-discharge rate of 0.1 C; FIG. 5 shows charge-discharge cycle performance curves of a lithium ion battery in Example 7 of the invention at a charge-discharge rate of 0.1 C.

COMPARISON EXAMPLE 2

The solvent of the non-aqueouselectrolyte is PC:DEC:DMC:$F_2MSEO_2M$=35: 30:30:5, LiPF6 has a concentration of 1 M, and the coin-shaped battery (2025) is assembled following the method in Example 7. The discharge-charge test of the battery is carried out in the Shenzhen Neware battery charge and discharge test system, with a charge-discharge voltage of 0-3 V. The battery in Example 7 is charged with a constant current of 0.1 C or 0.2 C, and then is discharge at a constant current, with the discharge rate of 0.1 C or 0.2 C. In addition, the cyclic voltammetry is carried out using Germany ZAHNER electrochemical workstation.

Figure 6:
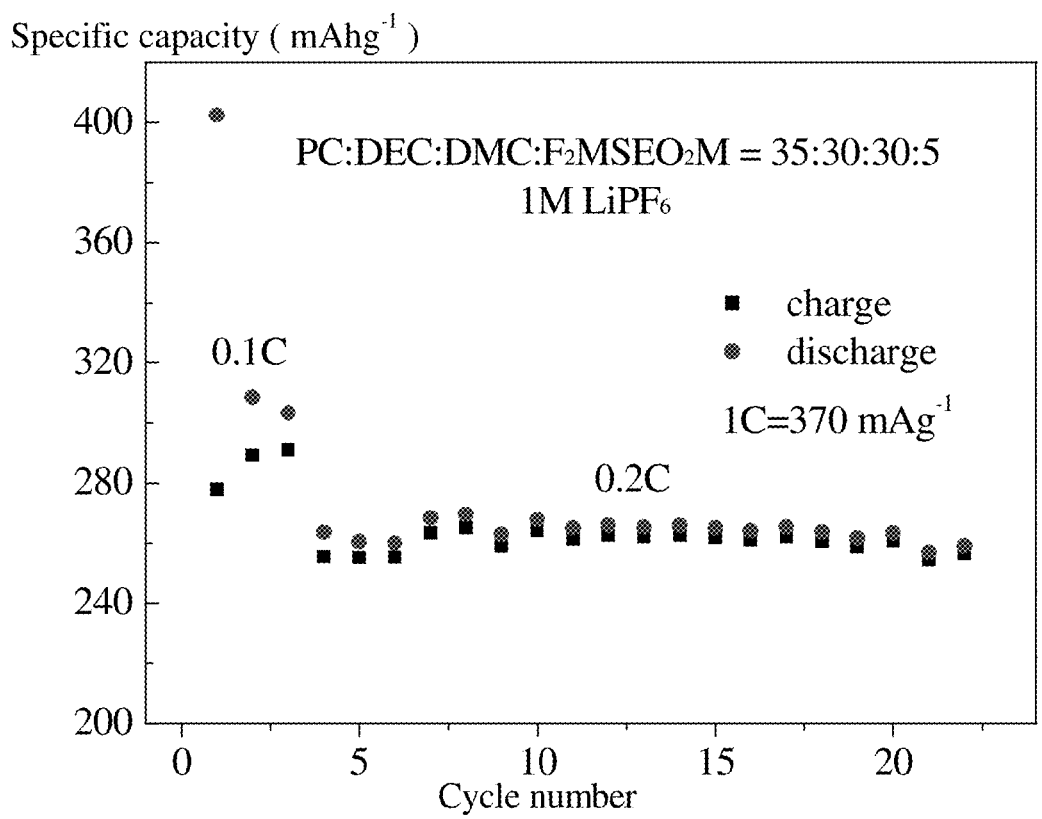
FIG. 6 shows charge-discharge cycle performance curves of a lithium ion battery in Comparison Example 2 of the invention at a charge-discharge rate of 0.1 C or 0.2 C, where the first three experiments are carried out at the charge-discharge rate of 0.1 C.

FIG. 6 shows charge-discharge cycle performance curves of a lithium ion battery in Comparison Example 2 of the invention at a charge-discharge rate of 0.1 C or 0.2 C.

The physical properties and electrochemical properties of the organohalosilane having a polyether chain are tested. $LiN(CF_3S_2O_2)_2$ is dissolved in a corresponding compound to yield an electrolyte solution with a concentration of 1 M. The ionic conductivities under different temperatures are measured using an ionic conductivity meter. Table 1 lists the comparison results of $F_2MSEO_2M$, $CDMSEN_2$ and $1S_3M_2$ (J. Mater. Chem., 20 (2010) 8224). All data are measured at room temperature.

TABLE 1

| Compound | Viscosity/ mPa · S | Dielectric constant | Ionic conductivity/ mS · cm$^{-1}$ | Electro-chemical window/V |
|---|---|---|---|---|
| $F_2MSEO_2M$ | 1.79 | 9.50 | 1.46 | 4.95 |
| $CDMSEN_2$ | 1.89 | 5.65 | — (Not measured) | — (Not measured) |
| $1S_3M_2$ | 2.10 | 4.44 | 0.90 | — (Not measured) |

Figure 2:
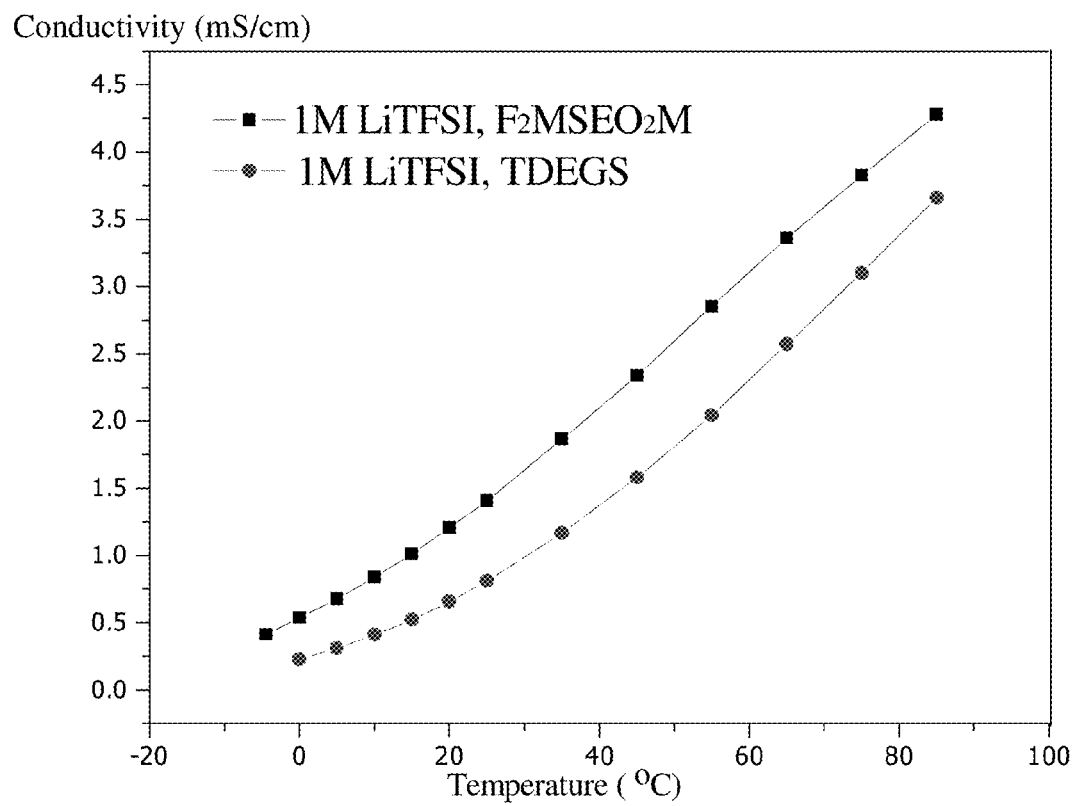
FIG. 2 shows curves of ionic conductivity of a compound in Example 2 under different temperatures (1M LiTFSI)

The difference between $F_2MSEO_2M$ and $1S_3M_2$ in chemical structure lies in the former contains two fluorine atoms instead of methyl. As shown in Table 1, the fluorine-containing compound $F_2MSEO_2M$ has a lower viscosity at room temperature and higher ionic conductivity. FIG. 1 shows the electrochemical window of $F_2MSEO_2M$ at room temperature which is 0-4.95 V. FIG. 2 shows curves of ionic conductivity of $F_2MSEO_2M$ under different temperatures. Based on the data, the organohalosilane having a polyether chain represented by formula I is suitable for use as a cosolvent of the electrolyte or an additive.

The polyether chain in the chemical structure provides a complexation site for lithium ions thereby facilitating the ion transport and improving the battery performance. The unit number of the polyether chain determines the viscosity of the material and the solubility of the lithium salt. Preferably, organohalosilane having two EO unit chains is selected, for example $F_2MSEO_2M$, which has a low viscosity and good solubility to lithium salt.

In example 7, the solvent of the electrolyte solution consists of PC and $F_2MSEO_2M$ with a ratio of 1:1, and the test whether the solvent can improve the SEI membrane properties of a graphite electrode is carried out. As shown in FIGS. 3 and 4, in the PC-based electrolyte, the application of $F_2MSEO_2M$ can effectively inhibit the co-embedment of the PC molecules into the graphite layer and allow them to be separated, thereby forming a stable SEI membrane on the surface of the graphite electrode. FIG. 5 shows charge-discharge cycle performance curves of a lithium ion battery in Example 7 of the invention at a charge-discharge rate of 0.1 C; the first discharge specific capacity of the battery is 462 mAh/g. After 20 cycles, the discharge specific capacity of the battery is 310 mAh/g. The conclusion is that, the battery maintains above 99% efficiency and has a stable cycle performance.

In Comparison Example 2, chain carbonates DEC and DMC are added to the electrolyte solution in Example 7, and thus, the concentrations of PC and $F_2MSEO_2M$ are decreased, thereby reducing the viscosity of the electrolyte solution. The mixture ratio is PC:DEC:DMC: $F_2MSEO_2M$=35:30:30:5. As shown in FIG. 6, although $F_2MSEO_2M$ is only 5%, a stable SEI membrane can still be formed on the surface of the graphite electrode, and the cycle performance is also stable.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A compound of formula I,

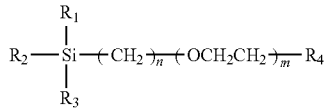

I wherein $R_1$, $R_2$, and $R_3$ independently, at each occurrence, represent:
  (a) —$(CH_2)_xCH_3$, where x is an integer from 0 to 5, or
  (b) F;

at least one of $R_1$, $R_2$, and $R_3$ is F;

$R_4$ is —$NR_5R_6$, wherein $R_5$ and $R_6$ independently, at each occurrence, represent a same or different $C_1$-$C_5$ alkyl;

m is an integer from 1 to 20; and n is an integer from 0 to 5.

2. A compound of formula I,

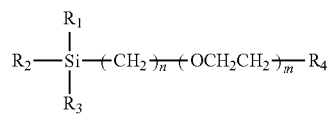

I wherein $R_1$, $R_2$, and $R_3$ independently represent:
  (a) —$(CH_2)_xCH_3$, where x is an integer from 0 to 5, or
  (b) a halogen, wherein the halogen is F or Cl;

at least one of $R_1$, $R_2$, and $R_3$ is the halogen;

$R_4$ is —$NR_5R_6$, wherein $R_5$ and $R_6$ independently represent $C_1$-$C_5$ alkyl;

m is an integer from 1 to 20; and n is an integer from 0 to 5.

* * * * *